(12) United States Patent
Blanc

(10) Patent No.: US 10,646,253 B2
(45) Date of Patent: May 12, 2020

(54) TROCAR STRUCTURE FOR ABDOMINAL SURGERY

(71) Applicant: AB MEDICA HOLDING S.R.L., Cerro Maggiore (MI) (IT)

(72) Inventor: Alexandre Blanc, Mery-sur-Cher (FR)

(73) Assignee: AB MEDICA S.P.A., Milan (IT)

( * ) Notice: Subject to any disclaimer, the term of this patent is extended or adjusted under 35 U.S.C. 154(b) by 129 days.

(21) Appl. No.: 15/748,181

(22) PCT Filed: Jul. 22, 2016

(86) PCT No.: PCT/EP2016/067538
§ 371 (c)(1),
(2) Date: Jan. 27, 2018

(87) PCT Pub. No.: WO2017/017015
PCT Pub. Date: Feb. 2, 2017

(65) Prior Publication Data
US 2018/0214178 A1 Aug. 2, 2018

(30) Foreign Application Priority Data

Jul. 29, 2015 (IT) .................. 102015000039254

(51) Int. Cl.
*A61B 17/34* (2006.01)
*A61M 39/06* (2006.01)
(Continued)

(52) U.S. Cl.
CPC ...... *A61B 17/3462* (2013.01); *A61B 17/0218* (2013.01); *A61B 17/34* (2013.01);
(Continued)

(58) Field of Classification Search
CPC . A61B 17/3498; A61B 17/0218; A61B 17/34; A61B 17/3462; A61B 2017/3464
See application file for complete search history.

(56) References Cited

U.S. PATENT DOCUMENTS 5,549,594 A * 8/1996 Brunken ............ A61B 1/00137
606/1
5,727,770 A 3/1998 Dennis
(Continued)

FOREIGN PATENT DOCUMENTS

EP 0541970 A1 5/1993
WO 97/43958 A1 11/1997
(Continued)

OTHER PUBLICATIONS

International Search Report for PCT/EP2016/067538 dated Sep. 26, 2016.

*Primary Examiner* — Ellen C Hammond
(74) *Attorney, Agent, or Firm* — Hedman & Costigan, P.C.; James V. Costigan; Kathleen A. Costigan

(57) ABSTRACT

The Trocar structure for abdominal surgery comprises a cannula having at one end a guide element provided with a valve for maintaining the positive intracavitary pressure and a shaft having, at one end a head and at the opposite end a tip, advantageously the valve is made of a single piece of silicone and has first elastically deformable sealing means for maintaining the positive intracavitary pressure during the passage of the shaft and of a surgical instrument through the cannula and second elastically deformable sealing means engaging the guide element.

4 Claims, 3 Drawing Sheets

(51) Int. Cl.
   A61B 17/02   (2006.01)
   A61M 39/22   (2006.01)
   A61M 39/24   (2006.01)
(52) U.S. Cl.
   CPC ...... A61B 17/3423 (2013.01); A61B 17/3498 (2013.01); A61M 39/06 (2013.01); A61M 39/22 (2013.01); *A61M 2039/064* (2013.01); *A61M 2039/0626* (2013.01); *A61M 2039/2426* (2013.01); *A61M 2039/2433* (2013.01)

(56) References Cited

U.S. PATENT DOCUMENTS

2013/0150792 A1* 6/2013 Alonso .............. A61B 17/3417
   604/167.01
2014/0222022 A1* 8/2014 Oberlaender ...... A61B 17/3462
   606/130

FOREIGN PATENT DOCUMENTS

WO          99/52577 A1   10/1999
WO   WO-2010045702 A1 *  4/2010  ......... A61B 17/3498

* cited by examiner

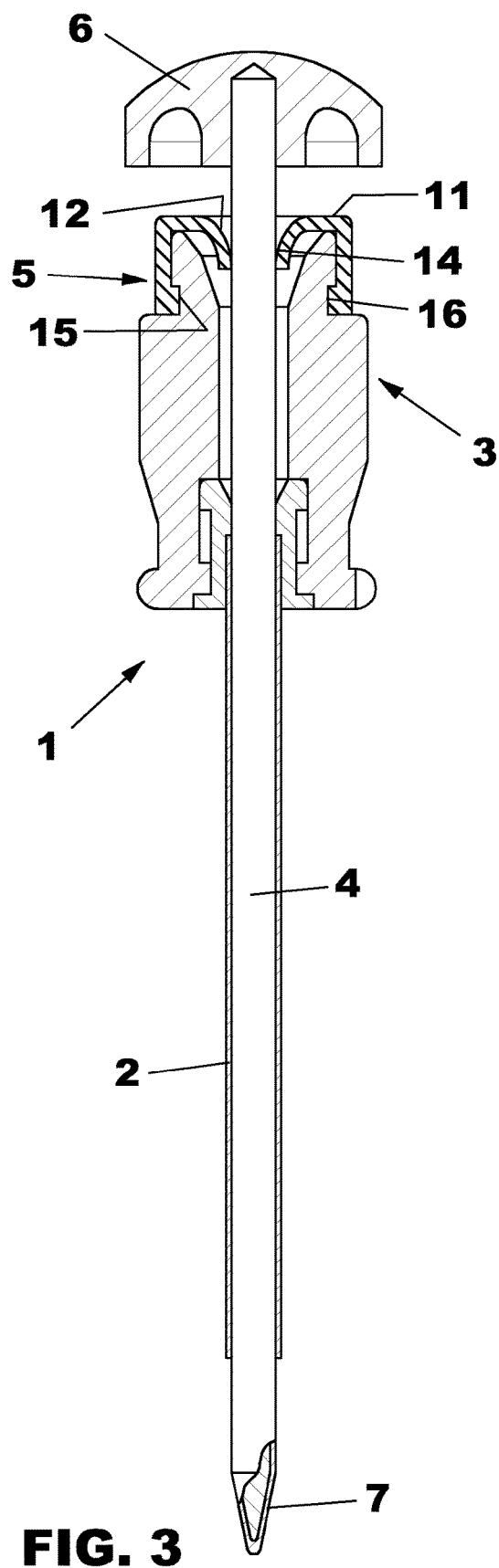
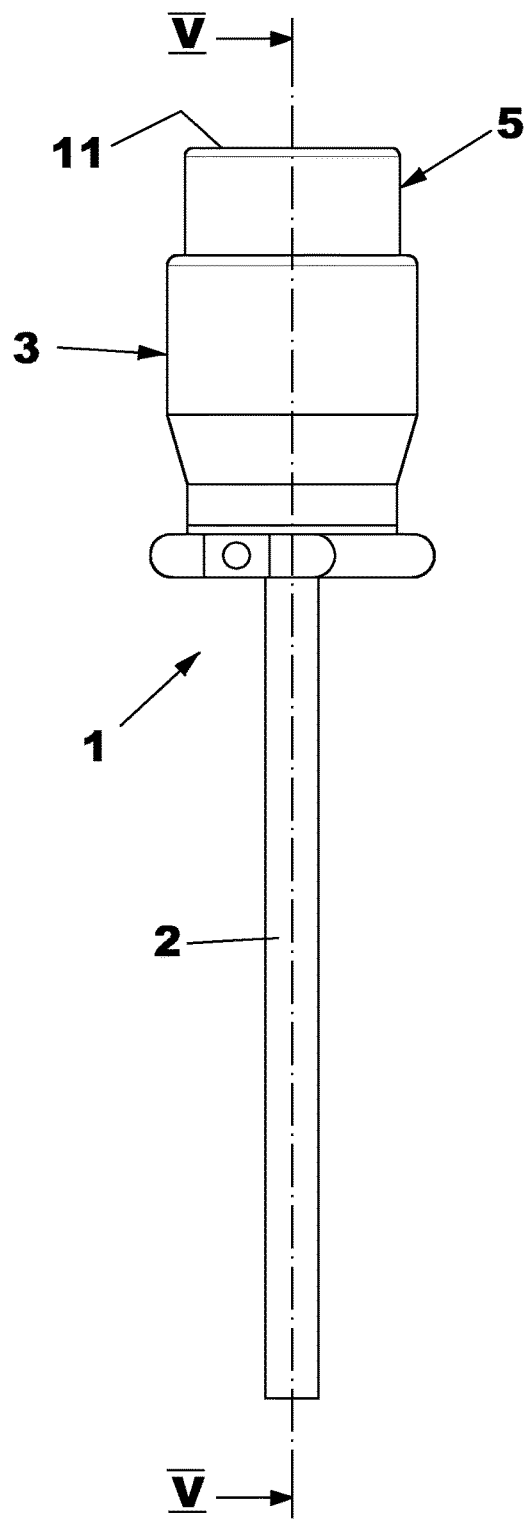
FIG. 3
FIG. 4

TROCAR STRUCTURE FOR ABDOMINAL SURGERY

The present invention relates to a Trocar structure for abdominal surgery.

As known, the trocars are surgical instruments suited to pierce the abdominal wall and that, after creating the pneumoperitoneum, it allows the passage of surgical instruments and, according to their diameter, have different gauges normally comprised between 2 mm and 15 mm.

All trocars having a greater diameter than those indicated are normally provided with reducers, which enable the use of even smaller diameter surgical instruments without any gas leakage.

Normally, trocars for this type of surgery are provided with a valve that allows for maintaining the positive intracavitary pressure unchanged and a retaining system for the abdominal wall so that the trocars cannot be dislocated during the continuous operations of introduction and extraction of the different instruments.

As can be gathered from the above, it is essential that during the passage of the various surgical instruments and extraction and replacement thereof, the valve for which each trocar is provided must always guarantee optimal sealing, and therefore maintain the positive intracavitary pressure at a predetermined value.

For this reason, the existing trocars normally have extremely expensive and complex valves that cannot be used and disposed of, as would be possible, with a disposable valve, but instead must be reused along with the trocars with all the consequences that the re-use of the instrumentation implies, for example, from the point of view of sterilization and structural conservation of the entire trocar.

Furthermore, as can be easily understood, the prolonged use of these valves does not always guarantee the reliability thereof and the replacement thereof involves replacing the entire trocar with considerable costs for the hospital institution that uses them.

The task proposed by the present invention is to produce a trocar structure for abdominal surgery provided with a disposable valve regardless of whether the trocar is reusable or disposable.

Within the context of this task, it is an object of the invention to produce a trocar structure for abdominal surgery having a disposable valve that always ensures a high degree of reliability.

A further object of the invention is to provide a Trocar structure for abdominal surgery with a valve having very low cost and, if necessary, can easily be replaced even by unskilled personnel.

A further object of the invention is to provide a trocar structure for abdominal surgery, with which the valve is able to signal the surgeon if the tip of the trocar is in the outer or inner position with respect to the cannula.

Another object of the invention to be underlined is to provide a trocar structure for abdominal surgery with a valve that performs an optimal sealing, thus allowing the introduction of instruments also in an initially angled manner.

This task, as well as these and other objects are achieved by a Trocar structure for abdominal surgery comprising a cannula (2) having at one end a guide element (3) provided with a valve (5) for maintaining positive intracavitary pressure and a shaft (4) having a head (6) at one end thereof and at the opposite end a tip (7), said valve being made of silicone in one single piece and has first elastically deformable sealing means (8) for maintaining said positive intracavitary pressure during the passage of said shaft (4) and of a surgical instrument through said cannula and second sealing means n, elastically deformable, with said guide element, characterized in that said first sealing means comprise central slits (10) oriented concentrically on a flat wall (11) of said disposable valve, said slits forming the lobes (12) adapted to bend internally or externally towards said wall in a uniform manner to form on the surface of said shaft (4) and of said surgical instrument a first collar (14) forming a continuous annular sealing and in that said second sealing means (9) comprise a second collar (15) engaging elastically an annular seat of said guide element.

Additional features are more detailed in the dependent claims which further specify the trocar structure and its disposable valve.

Object of the present invention is also a disposable valve having the features claimed in the claims 1-10 relating to the trocar structure.

Further characteristics and advantages of the invention will appear more evident from the description of a preferred but not exclusive embodiment of a trocar structure for abdominal surgery and of the associated valve, according to the invention, illustrated only by way of non-limitative example in the accompanying drawings, wherein:

FIG. 3 is a side elevation view of the cannula and along the section line A-A line of the trocar according to the invention;

FIG. 4 is a perspective view of the trocar valve according to the invention;

Figure 1:
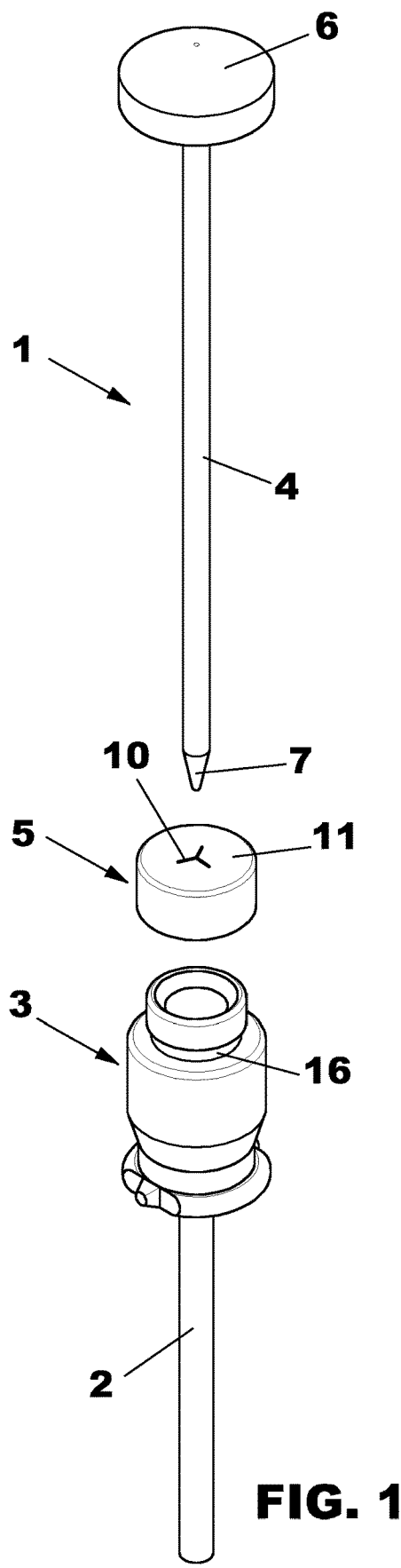
FIG. 1 is an exploded view of the trocar according to the invention.
Figure 2:
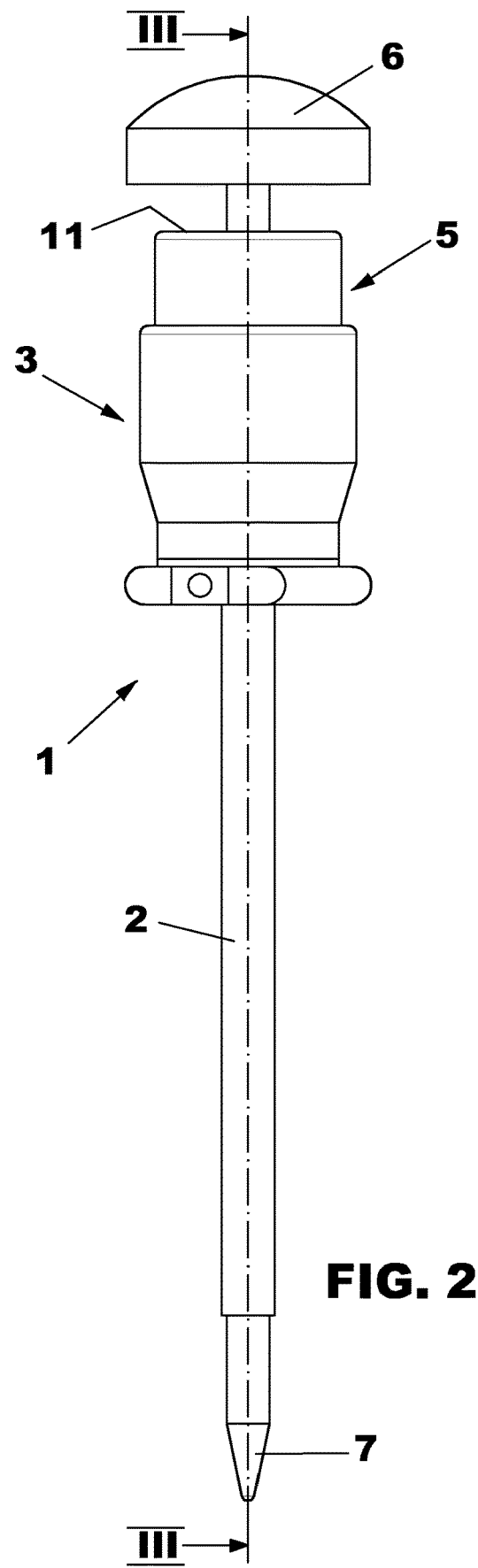
FIG. 2 is a side elevation view and along the section line A-A of the trocar according to the invention.
Figure 5:
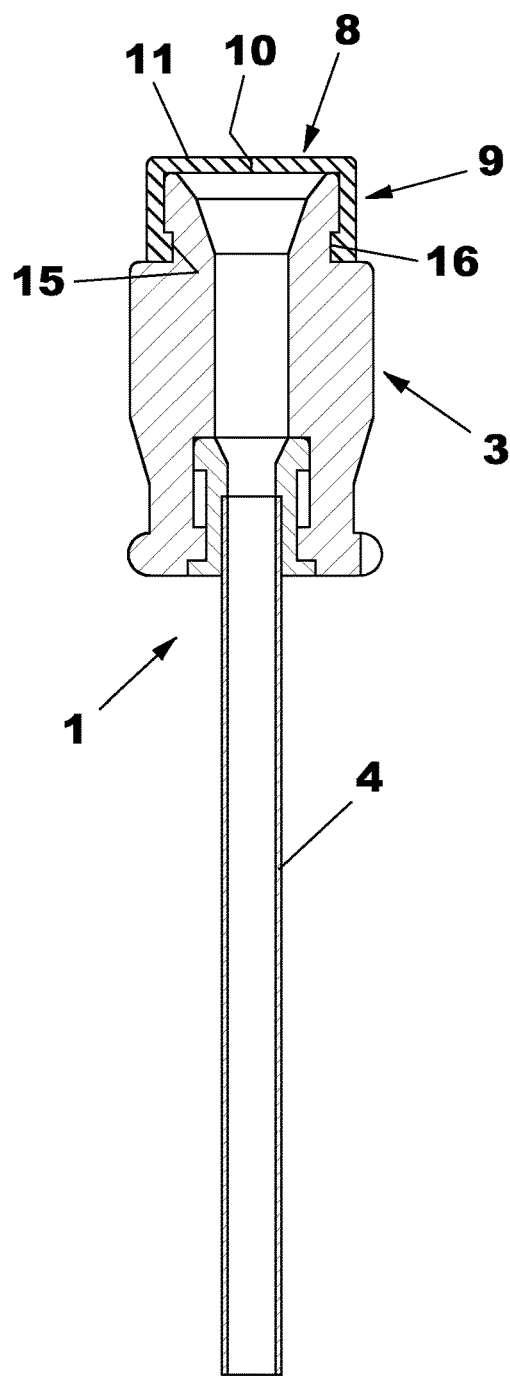
FIG. 5 is a transversely sectioned view of the valve of FIG. 4 according to the invention.
Figure 6:
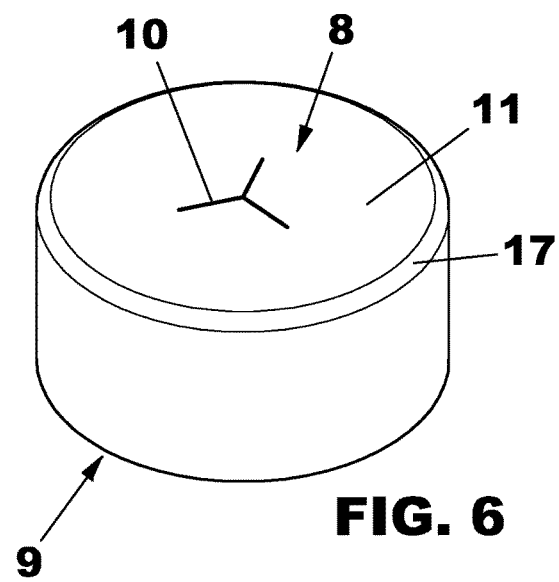
FIG. 6 is a plan view of the valve according to the invention.
Figure 7:
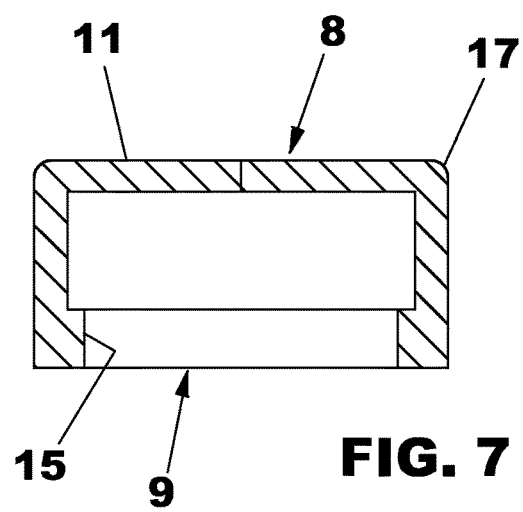
FIG. 7 is a transversely sectioned view of the valve of FIG. 6 according to the invention.
Figure 8:
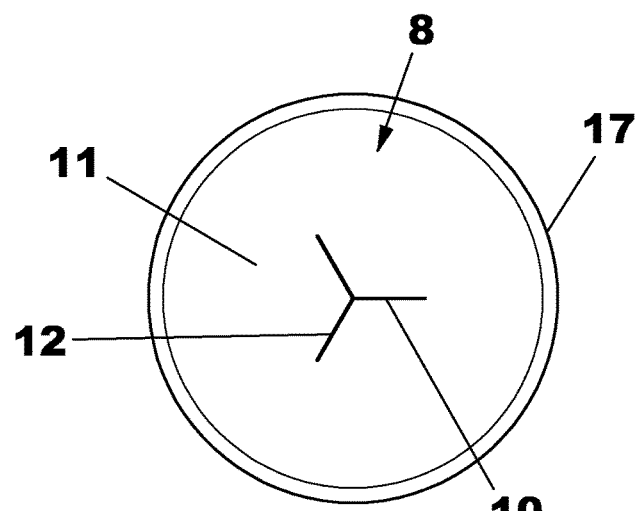
FIG. 8 is a top view of the valve of FIG. 6 according to the invention.

With particular reference to the figures described above, the trocar structure for abdominal surgery according to the invention is generally denoted with reference number 1.

In particular, the trocar structure 1 comprises a cannula 2 having at one end a guide element 3 of a pointed shaft 4.

To the guide element 3 a valve 5, for maintaining the positive intracavitary pressure, is associated in a removable manner.

The shaft 4 has at one end a head 6 and a tip 7 at the opposite end, and is internally slidable through the cannula 2.

Advantageously, the valve 5 is made of a single piece of silicone and therefore very easy to make, assemble and disassemble from the trocar.

In particular, the valve 5 has first sealing means, generally indicated with 8, which are elastically deformable for maintaining positive intracavitary pressure during the passage of the shaft 4 and of the surgical instruments necessary for the intervention, and not shown in the drawings, inside of the cannula 2.

The valve 5 has, furthermore, second sealing means, generically indicated with 9, also elastically deformable to perform the sealing with the guide element 3.

In particular, the sealing means 8 comprise central slits 10 oriented concentrically on the flat wall 11 of the valve in a manner adapted to form the lobes 12 suited to bend uniformly in opposite directions with respect to the flat wall 11 during the introduction and extraction of the shaft 4 and of the surgical instruments necessary for the surgery inside the cannula 2.

Advantageously, the length of each of the slits 10 is smaller than the radius of the flat wall 11 and of the diameter of the shaft 4.

In this way, when the lobes 12 are bent internally or externally with respect to the wall 11, they form on the surface of the shaft and on the surgical instruments a first collar 14 adapted to provide a continuous annular seal in both passage directions.

The slits 10 are arranged preferably at 120° and located only in a central portion of the flat wall 11 so that the remaining portion of the flat wall 11 has a surface sufficient to form the first collar 14, which sealingly surrounds an annular portion of the shaft 4, when it is inserted into the valve 5.

Said solution ensures, simultaneously, high sealing and elasticity characteristics together with a good technical strength as a function of the thickness of the valve wall.

Moreover, this solution ensures that, when the lobes 12 are arranged in a rest position, coplanar to one another, offer a bending resistance substantially equal to or greater than the force generated by said positive intracavitary pressure thus avoiding any loss thanks to the fact that the sealing of the lobes in the bent position and in the rest position is substantially equal.

During the extraction of the shaft 4 and the bending of the lobes 12 from a bent position towards the inside, to the one towards the outside with respect to the wall 11 an actual snap is determined informing the surgeon that the tip of the shaft is retracted inside the cannula.

In this way the surgeon is able to direct the trocar cannula in total safety knowing that the tip of the shaft no longer performs its function and therefore is not able to inflict any unintended lesions on the surrounding tissues.

The second sealing means 9 comprise a second collar which elastically engages an annular seat 16 provided on the guide element 3.

Advantageously, the collar 15 has a thickness greater than the thickness of the wall 11 and smaller than the height of the annular seat 16 so as to ensure an extreme ease of application of the valve into the trocar.

At last, it should also be stated that the flat wall 11 has a rounded circumferential edge 17 which directly connects the flat wall 11, which defines the entire top portion of the valve 5, with the cylindrical side wall at the end of which the collar 15 is provided.

The flat wall 11 and the cylindrical side wall of the valve 5 have, for reasons of safety and ease of production, a constant thickness adapted to exclude the use of a reducer during the use of the trocar.

An object of the present invention is also the single valve 5 which has the characteristic of being disposable in that numerous innovative structural and functional characteristics as mentioned above are comprised therewith.

The Trocar structure for abdominal surgery thus conceived is susceptible to numerous modifications and variations, all falling within the inventive concept and all details are replaceable by technically equivalent elements.

Practically, the materials used as well as the dimensions, may be any according to requirements and the state of the art.

The invention claimed is:

1. A Trocar structure for abdominal surgery comprising a cannula (2) having at one end a guide element (3) provided with a disposable valve (5) for maintaining positive intracavitary pressure and a shaft (4) having at one end a head (6) and at the opposite end a tip (7), said valve being made of a single piece of silicone and has first elastically deformable sealing means (8) for maintaining said positive intracavitary pressure during the passage of said shaft (4) and a surgical instrument through said cannula and second sealing means (9), elastically deformable, with said guide element, characterized in that said first sealing means comprise central slits (10) oriented concentrically on a flat wall (11) of said disposable valve (5), said slits forming lobes (12) adapted to bend inside or outside said wall in a uniform manner to form on the surface of said shaft (4) and of said surgical instrument, a first collar (14) providing a continuous annular seal and in that said second sealing means (9) comprise a second collar (15) engaging elastically an annular seat (16) of said guide element, said flat wall (11) defines an entire top portion of the disposable valve (5) and having a rounded circumferential edge (17) which directly connects said flat wall (11) with a cylindrical side wall at the end of which said second collar (15) is provided, said slits (10) being arranged preferably at 120° from one another and located only in a central portion of said flat wall (11) has a surface sufficient to form the first collar (14) which sealingly surrounds an annular portion of said shaft (4) when said shaft is inserted into the disposable valve (5), said flat wall (11) and said cylindrical side wall having a constant thickness adapted to exclude the use of a reducer during the use of the Trocar.

2. The Trocar structure according to claim 1, characterized in that said lobes (12), when they are in the rest position arranged coplanar to one another, offer a bending resistance substantially equal to or greater than the force generated by said positive intracavitary pressure.

3. The Trocar structure according to claim 1, characterized in that the seal of said lobes (12) in the bent position and in the rest position is substantially equal.

4. The Trocar structure according to claim 1, characterized in that said second collar (15) has a thickness greater than the thickness of said wall and less than the height of said annular seat (16).

* * * * *